United States Patent [19]

Ramioulle

[11] 3,993,671

[45] Nov. 23, 1976

[54] METHOD FOR THE CONTINUOUS DEHYDRATION OF MALEIC ACID

[75] Inventor: Jean Ramioulle, Bierghes, Belgium

[73] Assignee: U C B, Societe Anonyme, Belgium

[22] Filed: Aug. 27, 1974

[21] Appl. No.: 501,196

[30] Foreign Application Priority Data

Aug. 28, 1973 United Kingdom............... 40528/73

[52] U.S. Cl.......................................... 260/346.8 M
[51] Int. Cl.$^2$...................................... C07D 307/60
[58] Field of Search................................. 260/346.8

[56] References Cited
UNITED STATES PATENTS

| | | | |
|---|---|---|---|
| 2,688,622 | 9/1954 | Saquay............................ | 260/346.8 |
| 3,642,829 | 2/1972 | Weyent............................ | 260/346.8 |
| 3,865,849 | 2/1975 | Garlkish et al. ................. | 260/346.8 |

*Primary Examiner*—G. Thomas Todd
*Attorney, Agent, or Firm*—Wenderoth, Lind & Ponack

[57] ABSTRACT

A continuous process for the preparation of maleic anhydride from an aqueous solution of maleic acid formed in the production of maleic anhydride by the catalytic oxidation of aliphatic or aromatic hydrocarbons, with the continuous elimination of the impurities which accompany this maleic acid solution or which are subsequently formed in the course of the conversion of maleic acid into maleic anhydride.

4 Claims, 1 Drawing Figure

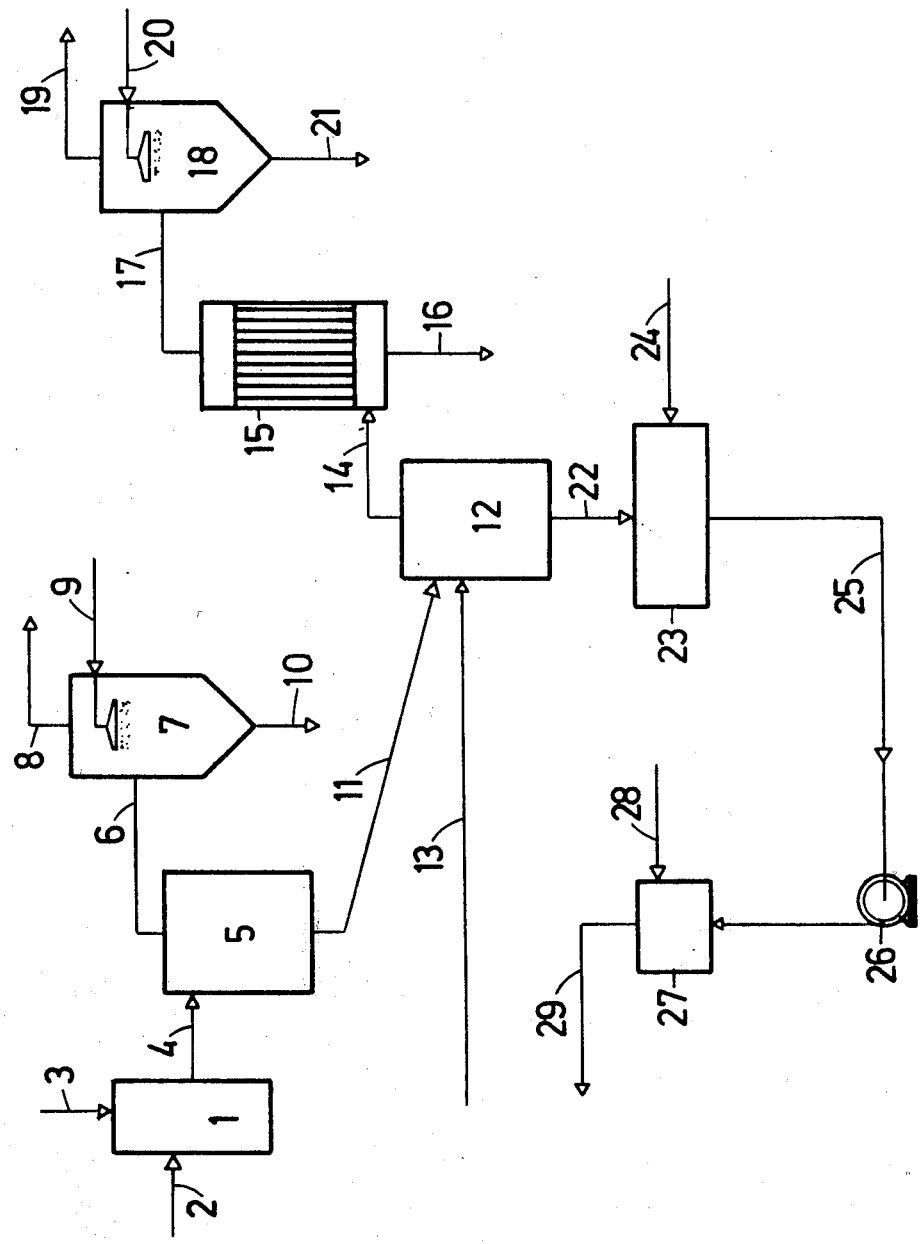

METHOD FOR THE CONTINUOUS DEHYDRATION OF MALEIC ACID

The present invention is concerned with a new method of dehydrating maleic acid to maleic anhydride by a continuous process and is also concerned with an apparatus for carrying out this new method. More particularly, the present invention is concerned with the recovery of maleic anhydride from an aqueous solution of maleic acid formed in the production of maleic anhydride by the catalytic oxidation of aliphatic and aromatic hydrocarbons, such as butane, butene and benzene.

In the effluent of a maleic anhydride synthesis reactor, the maleic anhydride vapors are very considerably diluted by a mixture of inert gases, such as nitrogen, unconsumed oxygen and the like. Although the vapor pressure of maleic anhydride at its melting point is only a few millimeters mercury, the dilution is such that at least 15% of the maleic anhydride leaving the reactor is not condensed by cooling and, therefore, can be recovered practically only by absorption in a solvent, generally water. In other words, in practically all processes actually used on an industrial scale, at least part of the synthetized maleic anhydride is finally in the form of an aqueous solution of maleic acid.

The reconversion of the (aqueous) solution of maleic acid into maleic anhydride by a continuous process encounters various difficulties, due to the presence of impurities. Some of these impurities originate from the reactor for the catalytic oxidation of hydrocarbons into maleic anhydride and comprise, for example, entrained catalyst, products of incomplete oxidation, such as benzoquinone, resinous materials and the like, the remainder of the impurities formed in the course of the actual reconversion of maleic acid into maleic anhydride comprising principally fumaric acid. All these impurities gradually accumulate in the apparatus in the course of time and the moment arrives when production must be stopped because clogging occurs and the transmission of heat becomes poorer and poorer because of the deposition of these impurities on the heat exchange surfaces. This cleaning operation is very laborious for the maintenance staff, while, in addition, the closing down of the installation constitutes a substantial loss of production and material.

In Belgian Patent No. 745,029, we have solved the problem of eliminating the impurities (fumaric acid, resins and the like) in a continuous process by a method consisting in only partly converting the maleic acid into the corresponding anhydride and treating the unconverted maleic acid, which entrains these impurities, with water in order, in this way, to form a solid phase composed of fumaric acid and other insoluble impurities and an aqueous liquid phase containing the dissolved maleic acid. The solid phase is eleminated from the system by filtration and the aqueous filtrate of maleic acid is recycled to the process. This process is satisfactory, provided that the operating criteria of the dehydrator for the partial conversion of maleic acid into the corresponding anhydride (dehydration pressure and temperature, residence time and the like) are scrupulously respected, these criteria varying, depending upon the freshness of the synthesis catalyst, the composition of the maleic acid subjected to dehydration and the like. It would be very advantageous to provide a process enjoying all the advantages of the process described in Belgian Patent No. 745,029, while possessing greater flexibility of operation. This is what constitutes the object of the present invention.

The present invention provides a continuous process for the preparation of maleic anhydride from an aqueous solution of maleic acid formed in the production of maleic anhydride by the catalytic oxidation of aliphatic or aromatic hydrocarbons, with the continuous elimination of the impurities which accompany this maleic acid solution or which are subsequently formed in the course of the conversion of maleic acid into maleic anhydride, which comprises the following stages:

a. continuously heating the starting aqueous solution of maleic acid in a concentration zone kept at a temperature of 100° to 150° C. and at a pressure of 400 to 760 mm.Hg. in order to obtain molten maleic acid containing 0 to 10% by weight of water and water vapor, and washing said water vapor in order to recover entrained maleic acid therefrom, the aqueous solution of maleic acid thus formed being fed to state (c);

b. continuously feeding the molten maleic acid obtained in stage (a) to a conversion zone kept at a temperature of 115° to 165° C. and at a pressure of 40 to 200 mm. Hg. and consisting of
   i. a liquid suspension composed of a reaction mixture containing about 1 to 20% by weight of maleic acid, 0 to 30% by weight of fumaric acid, 99 to 55% by weight of maleic anhydride and 0 to 5% by weight of resinous residues, and,
   ii. a purified gaseous phase containing maleic anhydride and water vapor, the amount of molten maleic acid added in an hour to the said reaction mixture representing from 10 to 50% of the weight of said reaction mixture;

c. continuously or semi-continuously withdrawing from 0.5 to 5% by weight of the said reaction mixture present in said conversion zone of step (c) per hour, and feeding it to a dissolution and filtration zone, in which it is suspended in the aqueous solution of maleic acid coming from stages (a) and (d), filtering the suspension thus obtained in order to separate a solid cake of fumaric acid and resinous residues, which is discharged from the system, and recycling a liquid filtrate consisting of an aqueous solution of maleic acid, to the starting aqueous solution of maleic acid;

d. continuously condensing the gaseous phase produced in stage (b) at a temperature above the dew point of the water vapor present, the condensate thus obtained being maleic anhydride with a purity of at least 99%, which is recovered as the product of the process, while washing with water the residual water vapor, which still contains entrained maleic anhydride, in order to form an aqueous solution of maleic acid, which is recycled to state (c).

By "starting aqueous solution of maleic acid" is meant the aqueous solution of maleic acid obtained by washing the reaction gases, either directly at the outlet of the synthesis reactor or at the outlet of the maleic anhydride condenser, when this device is used; furthermore, the starting aqueous solution of maleic acid comprises the aqueous solutions of maleic acid formed in stages (a), (c) and (d) of the process. In general, the total maleic acid titre of the starting aqueous solution of maleic acid is between about 250 and 500 g./liter.

By "resinous residues" are to be understood, in the context of the present invention, the various impurities existing in the system, with the exception of fumaric acid. These impurities comprise (1) the oxidation catalyst entrained from the synthesis reactor by the reaction gases, (2) products of partial oxidation of the hydrocarbon material used in the synthesis, for example benzoquinone, and (3) resinous products which are formed in the synthesis reactor and/or in the dehydration of the molten maleic acid in stage (b) of the process.

Stage (a)

The concentration zone mentioned in (a) may comprise one or more evaporator devices of any kind, however, preference is given to so-called thin layers evaporators. In this concentration zone, the temperature is kept between 100° and 150° C. and preferably at about 135° C., while the pressure is kept between 400 and 760 mm. Hg. and preferably at about 500 mm.Hg., in order to reduce the water content of the maleic acid to 0–10% by weight. For the good performance of the process, it is advantageous to lower the water content of the solution to the lowest possible value; dehydration may even be continued slightly beyond 100%, i.e. until the beginning of the conversion of maleic acid into maleic anhydride. The residence time of the maleic acid in the concentration zone is advantageously from 0.1 to 5 minutes and is preferably less than 1 minute. The partially or completely dehydrated maleic acid arrives at the outlet of the concentration zone in a liquid state and its temperature is between 125° and 150° C. Because of the moderate operating conditions applied in the concentration zone and because of the short residence time, the presence of fumaric acid in the maleic acid thus obtained is practically undetectable.

The water vapor eliminated during the concentration of the aqueous maleic acid solution into substantially anhydrous molten maleic acid entrains a certain amount of maleic acid. For this reason, the water vapor is passed into a washer in order to recover the entrained maleic acid; the aqueous solution of maleic acid obtained in this manner is used in stage (c).

Stage (b)

The molten maleic acid obtained in stage (a) is fed to the conversion zone (b) which comprises a large capacity still-dehydrator, i.e. a vessel provided with a supply pipe for molten maleic acid, heating means, a vaccum connection pipe which serves at the same time as pipe for the elimination of a vaporized mixture of water and maleic anhydride and a purge pipe for removing part of the reaction mixture contained in the still-dehydrator. The still-dehydrator may optionally contain agitation means and a maleic anhydride inlet pipe.

The still-dehydrator contains a reaction mixture, the composition of which must be maintained within limits which are critical for the good performance of the process. We have found that this reaction mixture must contain from 1 to 20% by weight of maleic acid, 99 to 55% by weight of maleic anhydride, 0 to 30% by weight of fumaric acid and 0 to 3% by weight of resinous residues. There are various ways of keeping the composition of the reaction mixture within the limits defined above. Thus, the percentage of maleic acid can be kept within the limits indicated by suitably adjusting the supply flow of molten maleic acid coming from stage (a); as a rule, when the reaction mixture has reached its stationary state within the composition limits indicated above, the hourly flow of molten maleic acid represents about 10 to about 50% of the weight of the reaction mixture in the still-dehydrator. In other words, the residence time of the molten maleic acid in the still-dehydrator is from 2 to 10 hours.

As the result of our investigations, we have found that a relationship also exists between the maleic acid content and the content of resinous residues in the reaction mixture, the maleic acid content increasing parallel with the increase of the content of resinous residues. This phenomenon appears to be connected with the fact that the resinous residues retard the conversion of maleic acid into maleic anhydride, while also reducing the heat exchange capacity of the still-dehydrator. As the resinous residues accumulate in the still-dehydrator in proportion as production proceeds, according to the present invention provision is made for continuously or discontinuously purging the still-dehydrator, the amount purged representing from 0.5 to 5% by weight of the reaction mixture per hour, so as to keep the content of resinous residues within the limits indicated above.

The fumaric acid which is formed in the still-dehydrator also accumulates in the apparatus in the same way as the resinous residues and it is for this reason that the purge effected in order to reduce the content of resinous residues serves at the same time to eliminate the excess of fumaric acid from the still-dehydrator, thus making it possible to keep the composition of the reaction mixture within the limits indicated above.

The maleic anhydride content of the reaction mixture is governed by the operating conditions, the latter preferably comprising a temperature between about 115 and about 165° C. and a pressure between about 40 and about 200 mm.Hg. when the stationary state of the composition of the reaction mixture has been reached. The maleic anhydride, which is continuously formed in the still-dehydrator at the expense of the maleic acid introduced, is eliminated in the form of a gaseous mixture of maleic anhydride and water.

Various methods are available for forming the reaction mixture. Thus, maleic acid from stage (a) can simply be added to the still-dehydrator until the latter is filled to its normal level; under the conditions of temperature and pressure prevailing in the still-dehydrator, the maleic acid is progressively converted into maleic anhydride and the introduction of maleic acid is finally so adjusted that the reaction mixture has the desired contents of maleic acid and maleic anhydride. As soon as the contents of fumaric acid and resinous residues of the mixture become too high, the continuous or discontinuous purging of the reaction mixture is effected in the manner explained above. Another possible procedure comprises introducing maleic anhydride of any origin into the still-dehydrator in advance and commencing the introduction of maleic acid coming from stage (a), while operating under the conditions of temperature and pressure specified above. Another way of forming the reaction mixture in the still-dehydrator consists in temporarily or continuously taking crude maleic anhydride from maleic anhydride condensers which are installed at the outlet of the synthesis reactor and feeding it to the still-dehydrator.

Stage (c)

Stage (c) of the process of the present invention deals with the elimination of the fumaric acid and resinous residues from the reaction mixture leaving the still-dehydrator in stage (b) through the purge pipe and, at the same time, recovering the maleic acid and- /or maleic anhydride contained in the purged reaction mixture.

For this purpose, the purged reaction mixture is passed into a mixer in which the aqueous solution of maleic acid produced in stages (a) and (d) is added. The maleic acid and/or maleic anhydride contained in the purged reaction mixture is or are dissolved, while the fumaric acid and resinous residues remains insoluble and the aqueous suspension thus formed is passed to a conventional filtration apparatus in order to separate it into a solid filter cake and a liquid filtrate. The filter cake, which contains the fumaric acid and the resinous products, is washed and then removed from the system as production residue; if desired, the removal of the fumaric acid from it may be contemplated. The filtrate, together with the filter cake washing liquid, consists of an aqueous solution of maleic acid, which is returned to the starting aqueous solution of maleic acid.

Stage (d)

The purified gaseous phase obtained in stage (b), which contains maleic anhydride and water vapour, is passed to a condensation zone in which, on the one hand, the maleic anhydride is condensed at a temperature higher than the dew point of the water vapour contained in this phase and, on the other hand, the uncondensed portion of the gaseous phase is washed with water in order to recover, in the form of an aqueous solution of maleic acid, the maleic anhydride which remains in the uncondensed portion. The maleic anhydride condensed in this condensation zone constitutes the product of the present invention; its purity is at least 99% and its fumaric acid content is from 0 to 0.1%. However, in order to give it the degree of purity and degree of stability required by commercial standards, this product can easily be treated by suitable well known methods, particularly by vacuum distillations. The aqueous solution of maleic acid obtained by washing the gaseous phase is, in turn, passed to stage (c) of the process for the dissolution of the purged reaction mixture.

The process according to the present invention, which has just been described, offers very considerable advantages over the prior art: in view of the fact that the impurities are continuously eliminated from the system, the process is truly continuous, in the sense that periodic cleaning of the installation for removal of incrustations caused by the accumulation of impurities is practically no longer required;

at the outlet of the installation, the maleic anhydride obtained by this process already has a purity of at least 99%, with a practically zero content of fumaric acid;

because the maleic anhydride and/or maleic acid is or are entirely recovered in stages (a), (c) and (d), in the form of an aqueous solution of maleic acid which is recycled to the starting aqueous solution of maleic acid, the only loss of raw material is the fraction of maleic acid converted into fumaric acid. As the formation of fumaric acid, per hour of production, amounts at most to 1.5% by weight of the starting maleic acid, the yield of maleic anhydride in the process of the present invention attains at least 98.5% of the theoretical value; moreover, the fumaric acid, which is thus recovered, after an eventual purification by any known means, may be used for example in the production of unsaturated polyesters, various esters and the like;

the considerable mass of reaction mixture in the still-dehydrator of stage (b) constitutes a thermal and chemical reserve, the fluctuations of which can easily be controlled, thus making it possible to achieve an entirely automatic operation of the installation;

because of the complete recycling of the washing liquids to the system, the problem of residual waters and pollution is reduced to a minimum, the only production residue being in practice the cake of fumaric acid and resinous residues produced in stage (c);

the performance of the process is flexible because it is possible to treat either a solution of maleic acid alone or a mixture of maleic acid solution and liquid maleic anhydride originating from maleic anhydride condensers (in this connection see the definition given previously of starting aqueous solution of maleic acid and the procedure for forming the reaction mixture in the still-dehydrator of stage (b));

this flexibility of the process makes it possible to treat not only products of the oxidation of benzene (in which case the condensation in solid or liquid form of the maleic anhydride at the outlet of the synthesis reactor is dependent on the overall economy of the investment and operation) but also products of the oxidation of butene or butane for which the possibility of condensation of maleic anhydride in solid or liquid form from these products is slight or non-existent.

In the accompanying drawing, one form of construction of an apparatus for carrying out the process of the present invention is shown diagrammatically.

Reference 1 indicates a washer containing the starting aqueous solution of maleic acid which is to be treated by the process of the present invention in order to recover the maleic anhydride. This solution is formed by washing the synthesis gas arriving through 2 either direct from a reactor (not shown) and, in this case, all the synthetized maleic anhydride is entirely converted into an aqueous solution of maleic acid, or is obtained from outlet gases of maleic anhydride condensers (not shown), and in this case liquid or solid maleic anhydride and an aqueous solution of maleic acid are, at the outset, produced simultaneously in the installation. The starting aqueous solution of maleic acid also contains aqueous solutions of maleic acid formed at various points in the installation (see below), which are recycled to the washer 1 through pipe 3. The starting aqueous solution of maleic acid is passed through pipe 4 to an evaporator 5, in which it is freed from practically all its water of dissolution by heating under reduced pressure ($T = 100°–150°$ C.; $P = 400–760$ mm.Hg.). There is thus formed a vapor phase which still contains a certain amount of maleic acid and which leaves the evaporator 5 through pipe 6 and passes into a barometric washer 7 connected to a vacuum source 8, while liquid for washing the vapour phase enters through pipe 9 and leaves through pipe 10. Molten maleic acid formed in the evaporator 5 is, in turn, passed through pipe 11 to a still-dehydrator 12 which contains a reaction medium comprising maleic acid, maleic anhydride, fumaric acid and resinous residues in the proportions indicated above. Maleic anhydride originating from maleic anhydride condensers (not shown) may optionally be introduced into the still-dehydrator 12 through pipe 13. In the still-dehydrator 12, which operates at elevated temperature and under vacuum ($T = 115°–165°$ C.; $P = 40–200$ mm.Hg.), there is formed a gaseous mixture of purified maleic anhydride and water which leaves through pipe 14 and passes into condenser 15, from which the maleic anhydride is withdrawn from the process through pipe 16, while the water vapor, which entrains a certain amount of maleic anhydride, leaves at the top of the condenser 15 through pipe 17 and enters a barometric washer 18 connected by pipe 19 to a vacuum source (not shown), while the washing liquid enters the barometric washer 18 through pipe 20 and leaves it through pipe 21.

In order to effect the continuous elimination of the fumaric acid and resinous residues which accumulate in the still-dehydrator 12, part of the reaction mixture is withdrawn through pipe 22 and passed into a mixer 23 into which there are introduced, through 24, the aqueous solutions of maleic acid formed, respectively, in the barometric washers 7 and 18. There is thus formed an aqueous suspension which is withdrawn through discharge pipe 25 by pump 26 and passed to a filter 27, in which there are separated a cake of fumaric acid and resinous residues, which is washed at least once with water supplied through pipe 28, and a filtrate composed of the liquid phase of the said suspension, together with the cake washing waters, and which consists of a maleic acid solution which is recycled through pipe 29 and the pipe 3 to the washer 1. The water supplied through the pipe 28 may be partly or entirely replaced by the aqueous solutions of maleic acid recovered from the barometric washers 7 and 18.

The following Examples are given for the purpose of illustrating the present invention, reference being made to the accompanying drawing:

EXAMPLE 1

A benzene oxidation reactor (not shown) produces 2000 moles maleic anhydride per hour, of which 1000 moles per hour are condensed by cooling the gases in condensers (not shown) and 1000 moles per hour are recovered, in the form of an aqueous solution of maleic acid, from the washer 1.

This washer is fed at 3 with an aqueous recycled solution originating from the barometric washers 7 and 18, which contains about 75 moles of recovered maleic acid per hour, together with 125 moles per hour of maleic acid, which are recovered from the purge circuit 22, 23, 25, 26, 27, 29, and 3.

As shown in the drawing, the aqueous solution originating from the barometric washers 7 and 18 serves to dissolve this purged material; after filtration, this solution, which contains 200 moles of maleic acid per hour, is recycled to the washer 1 through the pipes 29 and 3.

The evaporator 5 is thus fed with a concentrated solution containing 450 grams of maleic acid per liter, at the rate of 1200 moles per hour (1000 moles per hour coming from the washing of the gases leaving the maleic anhydride condensers and 200 moles per hour (125 + 75) recycled at 3).

The water vaporized from the aqueous solution of maleic acid at a temperature of 135° C. and under a pressure of 500 mm.Hg. in the evaporator 5 escapes through the pipe 6 and is condensed in the barometric washer 7, while the maleic acid, now containing only about 1% by weight of water, leaves at the base of the evaporator at a temperature of 135° C. and is passed through the pipe 11 to the still-dehydrator 12.

The latter, also receiving the 1000 moles per hour of maleic anhydride coming from the condensers (not shown) through the pipe 13, contains a weight of reaction mixture corresponding to four times the hourly quantity by weight of maleic anhydride produced by the reactor, i.e. 8000 moles, calculated as maleic anhydride. The still-dehydrator works at a pressure of 135 mm.Hg. and at a temperature of 135° C.

The condenser 15 condenses, at a temperature of 80° C., 2000 moles per hour of pure maleic anhydride, from which must be deducted the loss of the purge circuit, which as a maximum attains 1.5% by weight. The pure maleic anhydride obtained as product of the process is collected in the liquid state at the base of the condenser 15 through the pipe 16; its maleic anhydride content is 99.5% by weight, its fumaric acid content is practically zero and its content of other impurities is 0.4% by weight. The maleic anhydride thus obtained is passed, if necessary, to a distillation column (not shown) for the removal of the last traces of impurities and for stabilization.

The water vapor escaping at the top of the condenser 15 is passed through the pipe 17 to the barometric washer 18 connected to a vacuum source (not shown) in order to recover the traces of maleic anhydride entrained by the water vapor; the resulting aqueous solution of maleic acid is either recycled directly to the washer 1 or is preferably used for dissolving the purged product of the still-dehydrator 12, for which purpose it is passed through the pipe 24 to the mixer 23.

The composition of the reaction mixture contained in the still-dehydrator, which depends on the rate of dehydration and the amount of the purge effected at 22, amounts, as an average during the duration of the test, to about 5% maleic acid, about 15% fumaric acid, about 78% maleic anhydride and about 2% resinous residues by weight.

The purged material 22 is dissolved in the mixer 23 under vacuum and the insoluble material (fumaric acid and resinous residues) is separated on the filter 27, the filter cake being washed with water entering through 28.

For dissolution in the mixer 23, use is preferably made of the aqueous solution of maleic acid originating from the recoveries effected at the barometric washers 7 and 18. 200 moles of recovered acid per hour (125 moles originating from the suspension of the purged material and 75 moles originating from the barometric washers 7 and 18 are thus recycled through 29 and 3 to the washer 1.

The filter cake constitutes the loss suffered in the process of the present invention. This loss comprises the maleic acid which was not extracted from the cake by washing and the fumaric acid which was formed from the maleic acid in the course of the dehydration process; it amounts to 1.5%. The duration of the test described in this Example is 330 hours, which corresponds to about four times the length of the same test carried out without effecting the continuous purge according to the present invention. At the moment when the test was stopped, the contents of the various constituents of the reaction mixture in the still-dehydrator were still those indicated in this Example and did not justify suspension of production.

EXAMPLE 2

A butane oxidation pilot reactor (not shown) produces 23 kg of maleic anhydride per hour, of which 6 kg/hour are condensed by cooling the gases in condensers (not shown) and 17 kg/hour are recovered, in the form of an aqueous solution of maleic acid, from the washer 1.

This washer is fed at 3 with an aqueous recycled solution originating from the barometric washers 7 and 18, which contains about 4.11 kg of recovered maleic acid per hour, together with 5.79 kg/hour of maleic acid, which are recovered from the purge circuit 22, 23, 25, 26, 27, 29 and 3.

The aqueous solution originating from the barometric washer 7 via pipe 10 is passed through pipe 24 to dissolve the purged material in the mixer 23; a total of 9.90 kg of maleic acid per hour is recycled to the washer 1 through pipes 29 and 3.

The evaporator 5 is thus fed with a 38.5% by weight concentrated solution of maleic acid, at the rate of 30 kg per hour (20.1 kg/hour coming from the washing of the gases leaving the maleic anhydride condensers and 9.9 kg/hour recycled at 3).

The water vaporized from the aqueous solution of maleic acid at a temperature of 135° C and under a pressure of 500 mm.Hg. in the evaporator 5, escapes through the pipe 6 and is condensed in the barometric washer 7, while the maleic acid, now containing only about 1% by weight of water, leaves at the base of the evaporator at a temperature of 135° C. and is passed through the pipe 11 to the still-dehydrator 12.

The latter, also receiving the 6 kg/hour of maleic anhydride coming from the condensers (not shown) through the pipe 13, contains a weight of reaction mixture corresponding to four times the hourly quantity by weight of maleic anhydride produced by the reactor, i.e. 125 kg., calculated as maleic anhydride. The still-dehydrator works at a pressure of 135 mm.Hg. and at a temperature of 135° C.

The condenser 15 condenses, at a temperature of 80° C., 22.5 kg./hour of pure maleic anhydride. The pure maleic anhydride obtained as product of the process is collected in the liquid state at the base of the condenser 15 through the pipe 16; its maleic anhydride content is 99.5% by weight, its fumaric acid content is practically nil and its content of other impurities reaches 0.4% by weight. If necessary, the maleic anhydride thus obtained is passed to a distillation column (not shown) for the removal of the last traces of impurities and for stabilization.

The water vapor escaping at the top of the condenser 15 is passed through the pipe 17 to the barometric washer 18 connected through 19 to a vacuum source (not shown), in order to recover the traces of maleic anhydride entrained by the water vapor; the resulting aqueous solution of maleic acid is either recycled directly to the washer 1 or is preferably used for dissolving the purged product of the still-dehydrator, for which purpose it is passed through pipes 21 and 24 to the mixer 23.

The composition of the reaction mixture contained in the still-dehydrator, which depends on the rate of dehydration and the amount of the purge effected at 22, amounts, as an average during the duration of the test, to about 3% of maleic acid, about 30% of fumaric acid, about 66.5% of maleic anhydride and about 0.5% of resinous residues by weight.

The purged material 22 is dissolved in the mixer 23 under vacuum and the insoluble material (fumaric acid and resinous residues) is separated on the filter 27, the filter cake being washed with water entering through 28.

As indicated above, for dissolution in the mixer 23, use is made of the aqueous solutions of maleic acid originating respectively from the recoveries effected at the barometric washers 7 and 18. 9.9 kg/hour of recovered acid (5.79 kg/hour originating from the suspension of the purged material and 4.11 kg/hour from the barometric washers 7 and 18 are thus recycled through 29 and 3 to the washer 1.

The filter cake constitutes the loss suffered in the process of the present invention. This loss comprises the maleic acid which was not extracted from the cake by washing and the fumaric acid which was formed from the maleic acid in the course of the dehydration process; it amounts to 2%.

After 480 hours, at the moment when the test was stopped, the contents of the various constituents of the reaction mixture in the still-dehydrator were still those indicated in this Example and did not justify suspension of production.

I claim:
1. A continuous process for the preparation of maleic anhydride from an aqueous solution of maleic acid formed in the production of maleic anhydride by the catalytic oxidation of aliphatic or aromatic hydrocarbons, with the continuous elimination of the impurities which accompany this maleic acid solution or which are subsequently formed in the course of the conversion of maleic acid into maleic anhydride, which comprises the following stages:

a. continuously heating the starting aqueous solution of maleic acid in a concentration zone kept at a temperature of 100° to 150° C. and at a pressure of 400 to 760 mm.Hg. in order to obtain molten maleic acid containing 0 to 10% by weight of water and water vapor, and washing said water vapor in order to recover entrained maleic acid therefrom, the aqueous solution of maleic acid thus formed being fed to stage (c);

b. continuously feeding the molten maleic acid obtained in stage (a) to a conversion zone kept at a temperature of 115° to 165° C. and at a pressure of 40 to 200 mm.Hg. and said conversion zone containing
   i. a liquid suspension composed of a reaction mixture containing about 1 to 20% by weight of maleic acid, 0 to 30% by weight of fumaric acid, 99 to 55% by weight of maleic anhydride and 0 to 5% by weight of resinous residues, the composition of said suspension being continuously maintained, and,
   ii. a purified gaseous phase containing maleic anhydride and water vapor, the amount of molten maleic acid added in an hour to the said reaction mixture representing from 10 to 50% of the weight of said reaction mixture;

c. continuously or semi-continuously withdrawing from 0.5 to 5% by weight of the said reaction mixture per hour, and feeding it to a dissolution and filtration zone, in which it is suspended in the aqueous solution of maleic acid coming from stages (a) and (d), filtering the suspension thus obtained in order to separate a solid cake of fumaric acid and resinous residues, which is discharged from the system, and recycling a liquid filtrate consisting of an aqueous solution of maleic acid, to the starting aqueous solution of maleic acid;

d. continuously condensing the gaseous phase produced in stage (b) at a temperature above the dew point of the water vapor present, the condensate thus obtained being maleic anhydride with a purity of at least 99%, which is recovered as the product of the process, while washing with water the residual water vapor, which still contains entrained maleic anhydride, in order to form an aqueous solution of maleic acid, which is recycled to stage (c).

2. A process according to claim 1 wherein step (b) is performed in a still-dehydrator.

3. A process according to claim 2 wherein the residence time of the molten maleic acid in said still-dehydrator is from 2 to 10 hours.

4. A process according to claim 1 wherein the conversion zone in stage (b) is kept at a temperature of about 135° C.

* * * * *